US011419638B2

(12) United States Patent
Jackson

(10) Patent No.: US 11,419,638 B2
(45) Date of Patent: *Aug. 23, 2022

(54) PIVOTAL BONE ANCHOR ASSEMBLY WITH CANNULATED SHANK HAVING A PLANAR TOP SURFACE SURROUNDING AN INTERNAL DRIVE SOCKET

(71) Applicant: Roger P. Jackson, Prairie Village, KS (US)

(72) Inventor: Roger P. Jackson, Prairie Village, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 17/328,737

(22) Filed: May 24, 2021

(65) Prior Publication Data
US 2021/0275231 A1 Sep. 9, 2021

Related U.S. Application Data

(63) Continuation of application No. 16/904,816, filed on Jun. 18, 2020, now Pat. No. 11,013,537, which is a (Continued)

(51) Int. Cl.
A61B 17/70 (2006.01)
A61B 17/86 (2006.01)
A61B 90/00 (2016.01)

(52) U.S. Cl.
CPC ...... *A61B 17/7035* (2013.01); *A61B 17/7028* (2013.01); *A61B 17/7032* (2013.01);
(Continued)

(58) Field of Classification Search
CPC ............ A51B 17/7035; A51B 17/7028; A51B 17/7032; A51B 17/7037; A51B 17/8625;
(Continued)

(56) References Cited

U.S. PATENT DOCUMENTS 854,956 A 5/1907 Martin
2,243,717 A 5/1941 Godoy et al.
(Continued)

FOREIGN PATENT DOCUMENTS

DE 20207850 10/2002
WO WO 95/013755 5/1995

OTHER PUBLICATIONS

European Search Report, EP14189707.4, dated Feb. 25, 2015.

*Primary Examiner* — Eduardo C Robert
*Assistant Examiner* — Tara Rose E Carter
(74) *Attorney, Agent, or Firm* — Polsinelli PC

(57) ABSTRACT

A pivotal bone anchor assembly includes a receiver having an axial bore with an internal support surface adjacent a lower opening and a channel configured to receive a fixation rod, as well as a shank having a proximal end portion configured to be pivotally supported by the internal support surface with the shank extending downward through the lower opening. The proximal end portion includes a drive socket engageable by a drive tool, an upwardly-facing planar top surface surrounding and entirely peripheral to the drive socket, and a central bore extending from the drive socket to a distal tip configured to receive a guide wire. The assembly further includes an insert with an upper surface configured to receive the fixation rod and a lower surface configured to transfer a downward force toward the proximal end portion of the shank to lock the assembly, with the planar top surface of the shank remaining spaced apart from the lower surface of the insert so as to not directly receive the downwardly-directed force when the assembly is locked by a closure.

36 Claims, 6 Drawing Sheets

Related U.S. Application Data continuation of application No. 16/057,563, filed on Aug. 7, 2018, now Pat. No. 10,695,101, which is a continuation-in-part of application No. 15/419,740, filed on Jan. 30, 2017, now Pat. No. 10,039,571, which is a continuation of application No. 14/557,945, filed on Dec. 2, 2014, now Pat. No. 9,662,143, which is a continuation of application No. 13/815,054, filed on Jan. 28, 2013, now Pat. No. 8,900,272, which is a continuation of application No. 12/804,580, filed on Jul. 23, 2010, now Pat. No. 8,394,133, which is a continuation of application No. 11/522,503, filed on Sep. 14, 2006, now Pat. No. 7,766,915, which is a continuation-in-part of application No. 11/178,854, filed on Jul. 11, 2005, now Pat. No. 7,789,896.

(60) Provisional application No. 60/832,644, filed on Jul. 21, 2006, provisional application No. 60/736,112, filed on Nov. 10, 2005, provisional application No. 60/728,912, filed on Oct. 21, 2005, provisional application No. 60/725,445, filed on Oct. 11, 2005, provisional application No. 60/722,300, filed on Sep. 30, 2005, provisional application No. 60/655,239, filed on Feb. 22, 2005.

(52) U.S. Cl.
CPC ........ *A61B 17/7037* (2013.01); *A61B 17/864* (2013.01); *A61B 17/8625* (2013.01); *A61B 17/8685* (2013.01); *A61B 2090/037* (2016.02)

(58) Field of Classification Search
CPC .............. A51B 17/864; A51B 17/8685; A61B 2017/037
USPC .................................. 606/246–279, 300–328
See application file for complete search history.

(56) References Cited

U.S. PATENT DOCUMENTS

| | | | |
|---|---|---|---|
| 2,524,095 A | 10/1950 | Williams | |
| 2,531,892 A | 11/1950 | Reese | |
| 2,532,972 A | 12/1950 | Vertin | |
| 2,579,438 A | 12/1951 | Longfellow | |
| 2,669,896 A | 2/1954 | Clough | |
| 2,813,450 A | 11/1957 | Dzus | |
| 3,013,244 A | 12/1961 | Rudy | |
| 3,236,275 A | 2/1966 | Smith | |
| 3,254,602 A | 6/1966 | Beerman et al. | |
| 4,269,178 A | 5/1981 | Keene | |
| 5,020,519 A | 6/1991 | Hayes | |
| 5,209,753 A | 5/1993 | Biedermann et al. | |
| D346,217 S | 4/1994 | Sparker | |
| 5,443,467 A | 8/1995 | Biedermann et al. | |
| 5,672,175 A | 9/1997 | Martin | |
| 5,885,286 A | 3/1999 | Sherman et al. | |
| 5,961,517 A | 10/1999 | Biedermann et al. | |
| 6,010,503 A | 1/2000 | Richelsoph et al. | |
| 6,077,262 A | 6/2000 | Schlapfer et al. | |
| 6,139,549 A | 10/2000 | Keller | |
| 6,183,472 B1 | 2/2001 | Lutz | |
| 6,214,012 B1 | 4/2001 | Karpman et al. | |
| 6,248,105 B1 | 6/2001 | Schlapfer et al. | |
| 6,254,602 B1* | 7/2001 | Justis ................ | A61B 17/7032 606/272 |
| 6,273,888 B1 | 8/2001 | Justis | |
| 6,280,442 B1 | 8/2001 | Barker et al. | |
| 6,287,311 B1 | 9/2001 | Sherman et al. | |
| 6,302,888 B1 | 10/2001 | Mellinger et al. | |
| 6,440,133 B1 | 8/2002 | Beale et al. | |
| 6,488,681 B2 | 12/2002 | Martin et al. | |
| 6,530,929 B1 | 3/2003 | Justis et al. | |
| 6,540,749 B2 | 4/2003 | Schafer et al. | |
| 6,565,565 B1 | 5/2003 | Yuan et al. | |
| 6,635,059 B2 | 10/2003 | Randall et al. | |
| 6,648,888 B1 | 11/2003 | Shluzas | |
| 6,730,089 B2 | 5/2004 | Jackson | |
| 6,755,829 B1 | 6/2004 | Bono et al. | |
| 6,837,889 B2 | 1/2005 | Shluzas | |
| 6,911,030 B1 | 6/2005 | Vanacker et al. | |
| 6,932,822 B2 | 8/2005 | Oribe et al. | |
| 7,066,937 B2 | 6/2006 | Shluzas | |
| 7,087,057 B2 | 8/2006 | Konieczynski et al. | |
| 7,090,679 B2 | 8/2006 | Saint-Martin et al. | |
| 7,144,396 B2 | 12/2006 | Shluzas | |
| 7,160,300 B2 | 1/2007 | Jackson | |
| 7,211,086 B2 | 5/2007 | Biedermann et al. | |
| 7,250,052 B2 | 7/2007 | Landry et al. | |
| 7,377,923 B2 | 5/2008 | Purcell et al. | |
| 7,527,638 B2 | 5/2009 | Anderson et al. | |
| 7,547,318 B2 | 6/2009 | Birkmeyer et al. | |
| 7,604,655 B2 | 10/2009 | Warnick | |
| 7,618,444 B2 | 11/2009 | Shluzas | |
| 7,662,172 B2 | 2/2010 | Warnick | |
| 7,666,189 B2 | 2/2010 | Gerber et al. | |
| 7,686,835 B2 | 3/2010 | Warnick | |
| 7,708,763 B2 | 5/2010 | Selover et al. | |
| 7,722,654 B2 | 5/2010 | Taylor et al. | |
| 7,789,896 B2 | 9/2010 | Jackson | |
| 7,833,251 B1 | 11/2010 | Ahlgren et al. | |
| 7,862,587 B2 | 1/2011 | Jackson | |
| 7,985,242 B2 | 7/2011 | Forton et al. | |
| 8,034,084 B2 | 10/2011 | Landry et al. | |
| 8,066,739 B2 | 11/2011 | Jackson | |
| 8,075,592 B2 | 12/2011 | Landry et al. | |
| 8,075,599 B2 | 12/2011 | Johnson et al. | |
| 8,100,915 B2 | 1/2012 | Jackson | |
| 8,100,946 B2 | 1/2012 | Strasbaugh et al. | |
| 8,162,948 B2 | 4/2012 | Jackson | |
| 8,262,704 B2 | 9/2012 | Matthis et al. | |
| 8,377,067 B2 | 2/2013 | Jackson | |
| 8,403,962 B2 | 3/2013 | Jackson | |
| 9,050,148 B2 | 6/2015 | Jackson | |
| 9,101,415 B2 | 8/2015 | Jackson | |
| 9,173,682 B2 | 11/2015 | Jackson | |
| 9,216,039 B2 | 12/2015 | Jackson | |
| 9,265,534 B2 | 2/2016 | Jackson | |
| 9,265,535 B2 | 2/2016 | Jackson | |
| 9,265,536 B2 | 2/2016 | Jackson | |
| 9,265,537 B2 | 2/2016 | Jackson | |
| 9,271,767 B2 | 3/2016 | Jackson | |
| 9,532,815 B2 | 1/2017 | Jackson | |
| 9,585,701 B2 | 3/2017 | Jackson | |
| 9,636,151 B2 | 5/2017 | Jackson | |
| 9,662,143 B2 | 5/2017 | Jackson | |
| 9,662,151 B2 | 5/2017 | Jackson | |
| 9,788,868 B2 | 10/2017 | Jackson | |
| 9,808,292 B2 | 11/2017 | Jackson | |
| 9,918,751 B2 | 3/2018 | Jackson | |
| 9,924,982 B2 | 3/2018 | Jackson | |
| 10,039,571 B2 | 8/2018 | Jackson | |
| 10,166,049 B2 | 1/2019 | Jackson | |
| 10,258,391 B2 | 4/2019 | Jackson | |
| 10,299,835 B2 | 5/2019 | Jackson | |
| 10,485,588 B2 | 11/2019 | Jackson | |
| 10,507,047 B2 | 12/2019 | Jackson | |
| 10,543,020 B2 | 1/2020 | Jackson | |
| 10,653,460 B2 | 5/2020 | Jackson | |
| 10,695,101 B2* | 6/2020 | Jackson ............. | A61B 17/7032 |
| 10,874,437 B2 | 12/2020 | Jackson | |
| 11,000,314 B2 | 5/2021 | Jackson | |
| 11,013,537 B2* | 5/2021 | Jackson ............. | A61B 17/7035 |
| 2002/0026193 A1 | 2/2002 | Barker et al. | |
| 2002/0035366 A1 | 3/2002 | Walder et al. | |
| 2002/0091386 A1 | 7/2002 | Martin et al. | |
| 2002/0116001 A1 | 8/2002 | Schafer et al. | |
| 2002/0133154 A1 | 9/2002 | Saint-Martin | |
| 2002/0143341 A1* | 10/2002 | Biedermann ...... | A61B 17/7032 606/308 |
| 2003/0023240 A1 | 1/2003 | Amrein et al. | |

(56) References Cited

U.S. PATENT DOCUMENTS

| | | |
|---|---|---|
| 2003/0100904 A1 | 5/2003 | Biedermann |
| 2004/0143265 A1 | 7/2004 | Landry et al. |
| 2004/0167525 A1 | 8/2004 | Jackson |
| 2004/0172022 A1 | 9/2004 | Landry et al. |
| 2005/0131408 A1 | 6/2005 | Sicvol et al. |
| 2005/0149036 A1 | 7/2005 | Varieur et al. |
| 2005/0192573 A1 | 9/2005 | Abdelgany et al. |
| 2005/0216003 A1 | 9/2005 | Biedermann et al. |
| 2006/0036252 A1 | 2/2006 | Baynham et al. |
| 2006/0058788 A1 | 3/2006 | Hammer et al. |
| 2006/0079909 A1 | 4/2006 | Runco |
| 2006/0173454 A1 | 8/2006 | Spitler et al. |
| 2006/0241600 A1 | 10/2006 | Ensign et al. |
| 2007/0270813 A1 | 11/2007 | Garamszegi |
| 2011/0015678 A1 | 1/2011 | Jackson |
| 2011/0060344 A1 | 3/2011 | Sicvol et al. |
| 2012/0071886 A1 | 3/2012 | Jackson |
| 2015/0080974 A1 | 3/2015 | Jackson |
| 2017/0181775 A1 | 6/2017 | Jackson |
| 2018/0132910 A1 | 5/2018 | Jackson |
| 2018/0146991 A1 | 5/2018 | Jackson |
| 2018/0168702 A1 | 6/2018 | Jackson |
| 2019/0090918 A1 | 3/2019 | Jackson |
| 2019/0209218 A1 | 7/2019 | Jackson |
| 2020/0069343 A1 | 3/2020 | Jackson |
| 2020/0237414 A1 | 7/2020 | Jackson |
| 2021/0137567 A1 | 5/2021 | Jackson |
| 2021/0161564 A1 | 6/2021 | Jackson |
| 2021/0259744 A1 | 8/2021 | Jackson |
| 2021/0338295 A1 | 11/2021 | Jackson |
| 2021/0361323 A1 | 11/2021 | Jackson |

\* cited by examiner

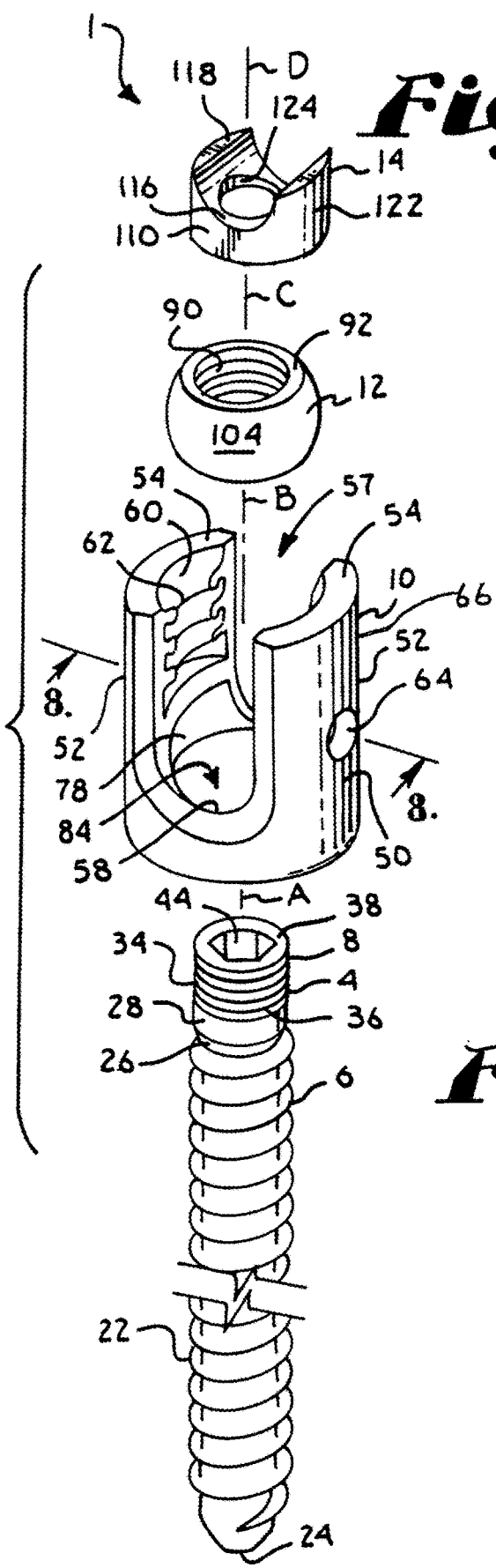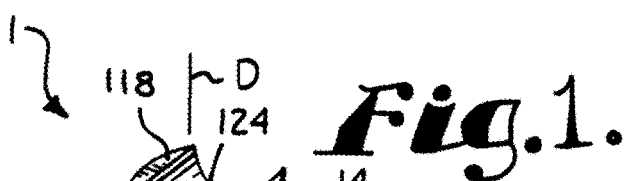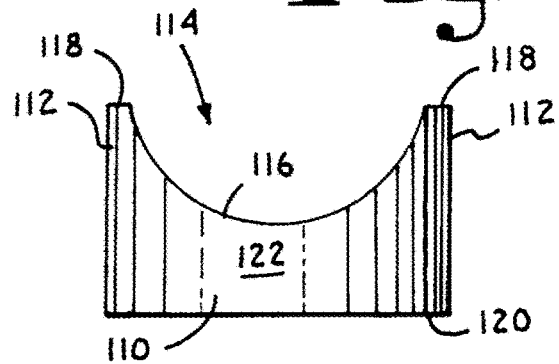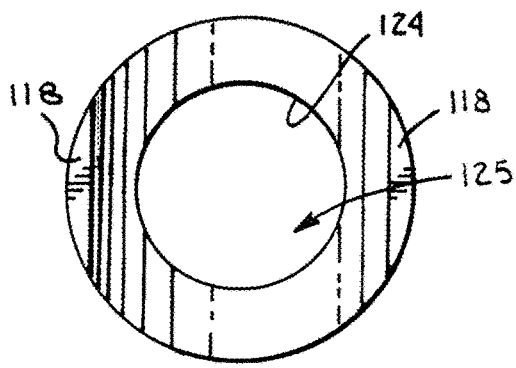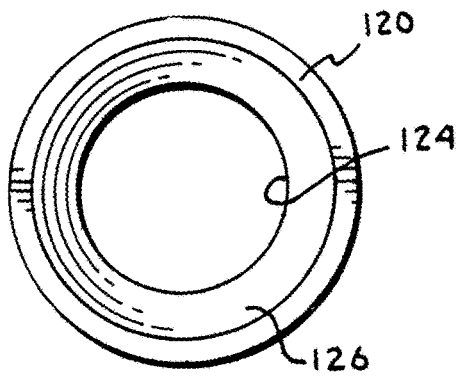

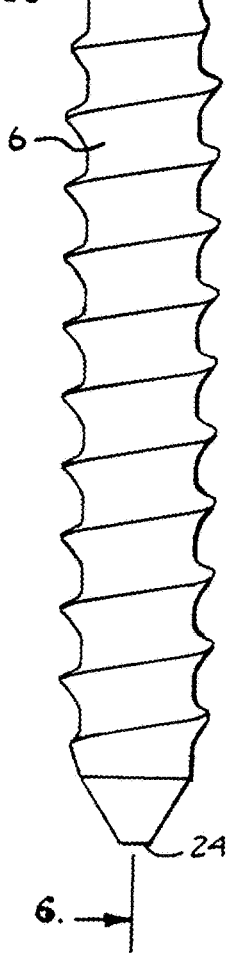
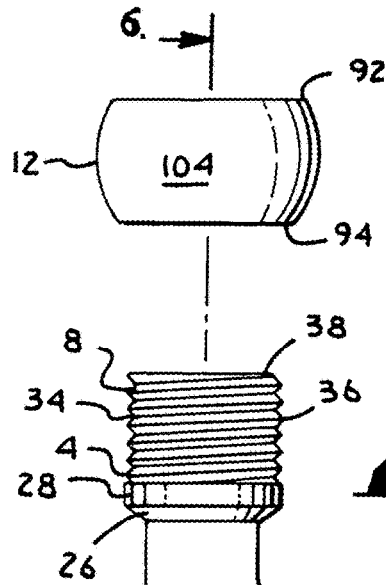
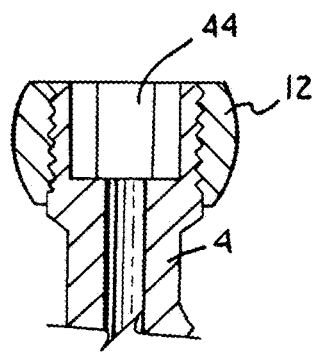
Fig.5.
Fig.6.
Fig.7.

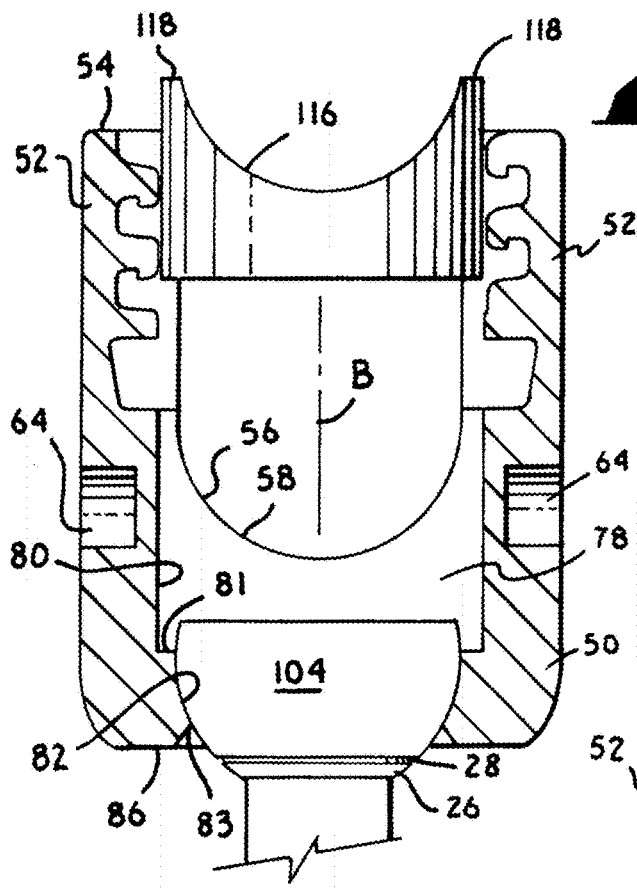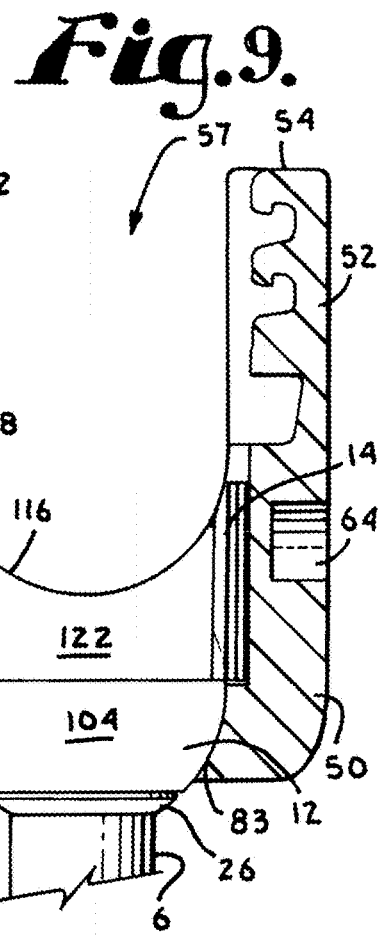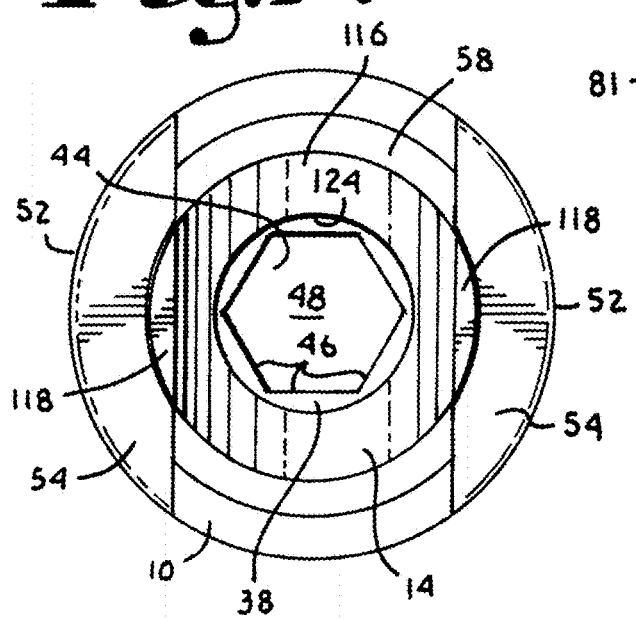

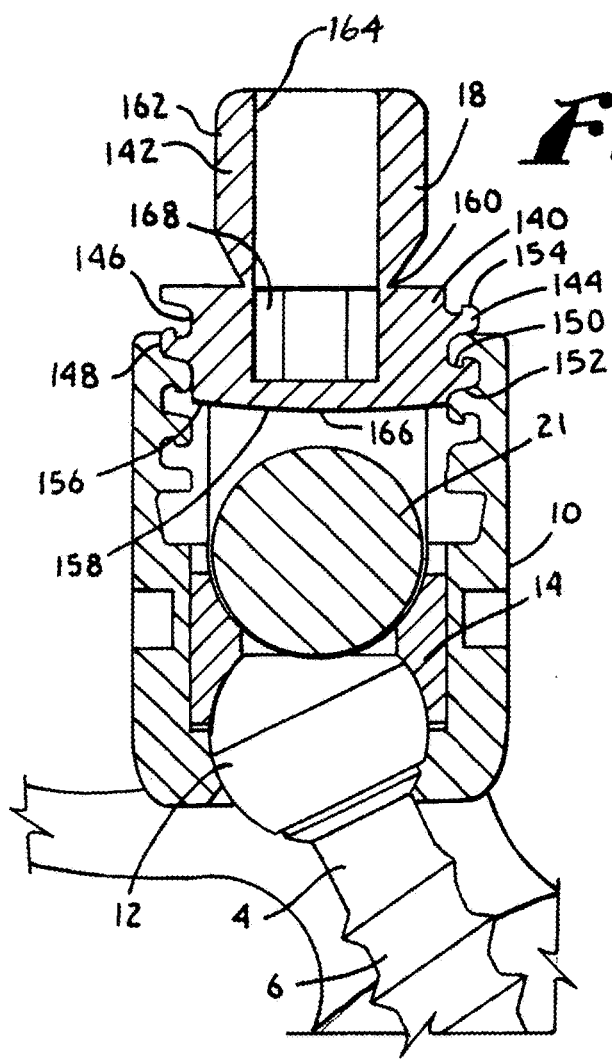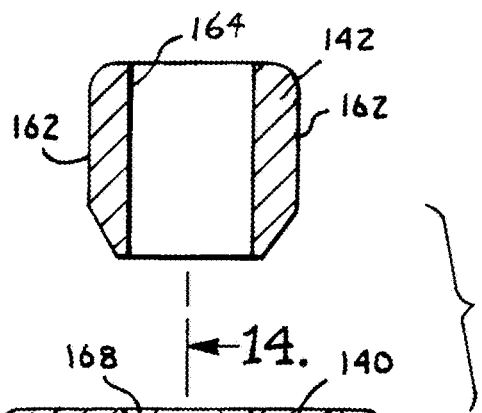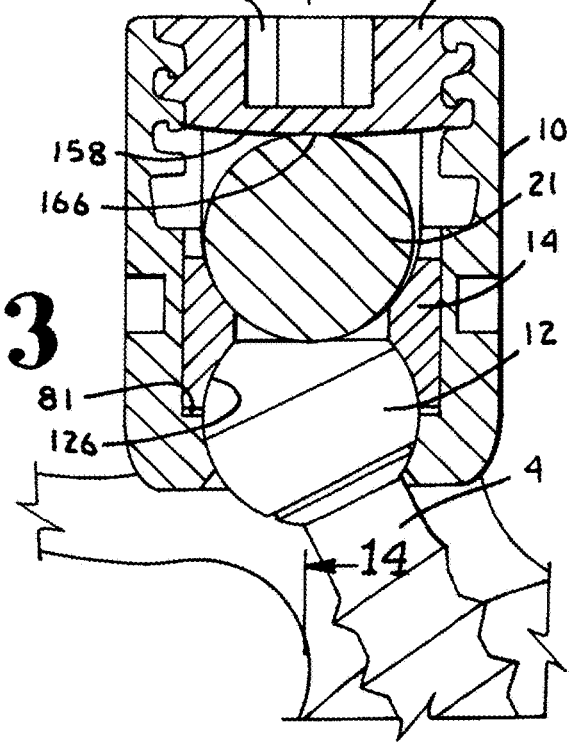

PIVOTAL BONE ANCHOR ASSEMBLY WITH CANNULATED SHANK HAVING A PLANAR TOP SURFACE SURROUNDING AN INTERNAL DRIVE SOCKET

CROSS REFERENCE TO RELATED APPLICATIONS

This application is a continuation of Application No. 16/904,816, filed Jun. 18, 2020, which is a continuation of application Ser. No. 16/057,563 filed Aug. 7, 2018, now U.S. Pat. No. 10,695,101, which is a continuation-in-part of application Ser. No. 15/419,740, filed Jan. 30, 2017, now U.S. Pat. No. 10,039,571, which is a continuation of application Ser. No. 14/557,945, filed Dec. 2, 2014, now U.S. Pat. No. 9,662,143, which is a continuation of application Ser. No. 13/815,054, filed Jan. 28, 2013, now U.S. Pat. No. 8,900,272, which is a continuation of application Ser. No. 12/804,580, filed Jul. 23, 2010, now U.S. Pat. No. 8,394,133, which is a continuation of application Ser. No. 11/522,503, filed Sep. 14, 2006, now U.S. Pat. No. 7,766,915, which claims the benefit of the following Provisional Applications: No. 60/832,644, filed Jul. 21, 2006; No. 60/736,112, filed Nov. 10, 2005; No. 60/728,912, filed Oct. 21, 2005; No. 60/725,445, filed Oct. 11, 2005; and No. 60/722,300, filed Sep. 30, 2005, each of which is incorporated by reference in its entirety herein and for all purposes.

application Ser. No. 11/522,503 is also a continuation-in-part of application No. 11/178,854, filed Jul. 11, 2005, now U.S. Pat. No. 7,789,896, which claims benefit of U.S. Provisional Application No. 60/655,239, filed Feb. 22, 2005, each of which is incorporated by reference in its entirety herein and for all purposes.

BACKGROUND OF THE INVENTION

The present invention is directed to polyaxial bone screws for use in bone surgery, particularly spinal surgery.

Bone screws are utilized in many types of spinal surgery, such as for osteosynthesis, in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be Laid or urged onto the open receiver channel of an open ended bone screw.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as a rod, or are supported by such a rod. Bone screws of this type may have a head or receiver that receives the rod or other structure that is fixed relative to a shank thereof. In the fixed bone screws, the fixed receiver cannot be moved relative to the shank and the rod must be favorably positioned in order for it to be placed within the receiver. This is sometimes very difficult or impossible to do. Therefore, polyaxial bone screws are commonly preferred.

Open-ended polyaxial bone screws allow rotation of a rod receiver with respect to the shank until a desired rotational position of the receiver is achieved relative to the shank. A rod is inserted into the receiver and eventually the receiver is locked or fixed in a particular position relative to the shank.

There are a variety of ways in which the rod may be captured within an open polyaxial bone screw. Some sort of closure structure or plug is required so as to block the channel opening once the rod is inserted therein and, also preferably urge the rod into a seated and locked position relative to the receiver. A substantial amount of torque is required to seat the plug against the rod which in turn. seats the rod in the receiver channel so as to prevent relative motion between the rod and the bone screw. Consequently, the need to highly torque a plug disposed between the arms of an open bone screw functions counter to the need to prevent the bone screw arms from splaying.

Certain prior art plug type closures have been threadably received between the opposed arms of the bone screw receiver using conventional V-shaped thread forms which has resulted in a significant amount of radially outward pressure or force being applied to the arms of the bone screw receiver. Such outward force may result in splaying of the arms, after which the closure becomes loose which may either result in a failure of the implant by allowing the rod to slip relative to the bone screw or the closure may even come completely out of the receiver of the bone screw for total failure of the implant. In order to help relieve this problem, certain of the prior art has added structure to the rod engaging lower surface of the closure. Such structure has included adding a central or axial point or ring designed to penetrate into the rod and help lock the rod into place. Surface finish on the plug, such as knurling, has also been utilized.

At a side of the rod opposite of the closure plug, various compression spacers or insertable compression structures have been developed that are operably disposed adjacent the rod and within the bone screw receiver. Such compression structures have been used to frictionally link the rod with the bone screw shank and to aid in snugly seating the rod in the open bone screw, thus aiding in preventing relative motion between the rod and the bone screw. Prior art bone screw compression inserts have typically been utilized with top-loaded bone screw shanks, having substantially spherical heads that are integral with the shank body. Such compression inserts include those that contact an upper spherical portion of the bone screw shank and others that extend substantially around such a spherical surface. Such compression inserts may also include a curved upper surface or surfaces for receiving the rod.

Bone screw compression inserts may desirably reduce relative motion between the rod and the bone screw, but may be undesirable in practice as they may also require separate insertion during surgery, after implantation of the bone screw shank, and may be small and thus difficult to handle. Alternatively, compression inserts loaded in a bone screw prior to implantation may obstruct bone screw features utilized for driving the threaded bone screw shank into bone, or require less than desirable modifications in the bone screw, decreasing strength and/or requiring specialized driving tools.

SUMMARY OF THE INVENTION

A polyaxial bone screw assembly according to the invention includes a shank having an upper portion and a body for fixation to a bone. The shank upper portion has a width or diameter smaller than a diameter of a lower opening of a cooperating receiver that also includes an open channel for receiving a rod or other elongate structure. The assembly further includes an independent non-integral retaining and articulating structure for attachment to the shank upper portion within the receiver. Furthermore, a compression structure is operably disposed between the retaining and articulating structure and the rod. The shank is connected to the receiver by the retaining and articulating structure that is operably slidably mated with an inner surface of the receiver, allowing the shank body to be swivelable with respect to the receiver.

According to one aspect of the invention, a closure member having a flangeform thereon is mateable with cooperating flange-form structure on inner arms of an upper portion of the receiver. The closure member further includes a dome-shaped lower surface for operably pressing against the rod or other structural member. The rod in turn contacts and presses on the compression structure and the compression structure contacts and presses on the retaining and articulating structure which fixes the retaining and articulating structure against an inner seating surface of the receiver.

According to another aspect of the invention, a bone screw shank upper portion is sized and shaped to be insertable through a lower opening of a receiver. The shank upper portion includes a helical thread and in some embodiments a lateral projection. In a particular embodiment the projection is in the form of a cylinder forming a buttress stop. The retaining and articulating structure includes a through-bore defined in part by a helical thread sized and shaped to mate with the helical thread of the shank capture structure. The retaining and articulating structure also includes structure, such as a cooperating buttress stop sized and shaped to abut against the projection when fully installed on the shank upper portion, stopping the retaining and articulating structure from further rotation down the shank upper portion. The retaining and articulating structure could have a vertical slit and thus be down-loadable or up-loadable into the receiver.

According to another aspect of the invention, the shank upper portion that is insertable in the receiver lower opening includes a driving formation at a top surface thereof. The driving formation is sized and shaped to receive an end of a driving tool. A further aspect of the invention includes a compression structure or insert that is pre-loadable in the bone screw receiver and includes a central through bore, allowing for the driving of the shank into bone with the insert loaded in the bone screw receiver. The insert in some embodiments can be down-loaded or up-loaded into the receiver, in particular the insert and the retaining structure could both be up-loaded into the receiver.

OBJECTS AND ADVANTAGES OF THE INVENTION

Therefore, objects of the present invention include: providing an improved spinal implant assembly for implantation into vertebrae of a patient; providing such an assembly that includes a receiver with an open channel, a shank pivotally connected to the receiver, a rod or other structural element, and a compression structure disposed between the shank and the rod for holding the shank at a desired angle of inclination or articulation with respect to the receiver; providing such an assembly that has a low profile after final installation; providing such an assembly in which the compression structure may be inserted into a bone screw receiver prior to installing the bone screw into bone; providing such an assembly in which an upper shank portion of the bone screw includes a non-slip feature for driving the shank into bone; providing such an assembly in which an upper portion of the bone screw shank has a maximum diameter or width that is smaller than a diameter or width of a lower opening of the bone screw receiver and further includes an independent retaining and articulating structure fixable to the shank upper portion within the bone screw receiver; and providing such an assembly that is easy to use, especially adapted for the intended use thereof and wherein the implant assembly components are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of an assembly according to the invention including a shank with a capture structure at one end thereof, a receiver, a retaining and articulating structure and a compression structure.

FIG. 2 is an enlarged front elevational view of the compression structure of FIG. 1.

FIG. 3 is an enlarged top plan view of the compression structure of FIG. 1.

FIG. 4 is an enlarged bottom plan view of the compression structure of FIG. 1.

FIG. 5 is an enlarged, exploded front elevation of the shank and retaining and articulating structure of FIG. 1.

FIG. 6 is a partial cross-sectional view of the shank and retaining and articulating structure taken along the line 6-6 of FIG. 5.

FIG. 7 is an enlarged and partial view of the shank and retaining and articulating structure of FIG. 6.

FIG. 8 is an enlarged and partial cross-sectional view of the receiver taken along the line 8-8 of FIG. 1 and showing a first stage of insertion of the compression structure.

FIG. 9 is an enlarged and partial cross-sectional view of the receiver similar to FIG. 8 and showing a fully installed compression structure.

FIG. 10 is a top plan view of the bone screw receiver, shank, retaining and articulating structure and compression structure of FIG. 9.

FIG. 12 is a partial cross-sectional view similar to FIG. 11 further showing a rod and a partially installed closure structure, also in cross-section.

FIG. 13 is a partial cross-sectional view similar to FIG. 12 showing a break-off head of the closure structure removed.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 11:
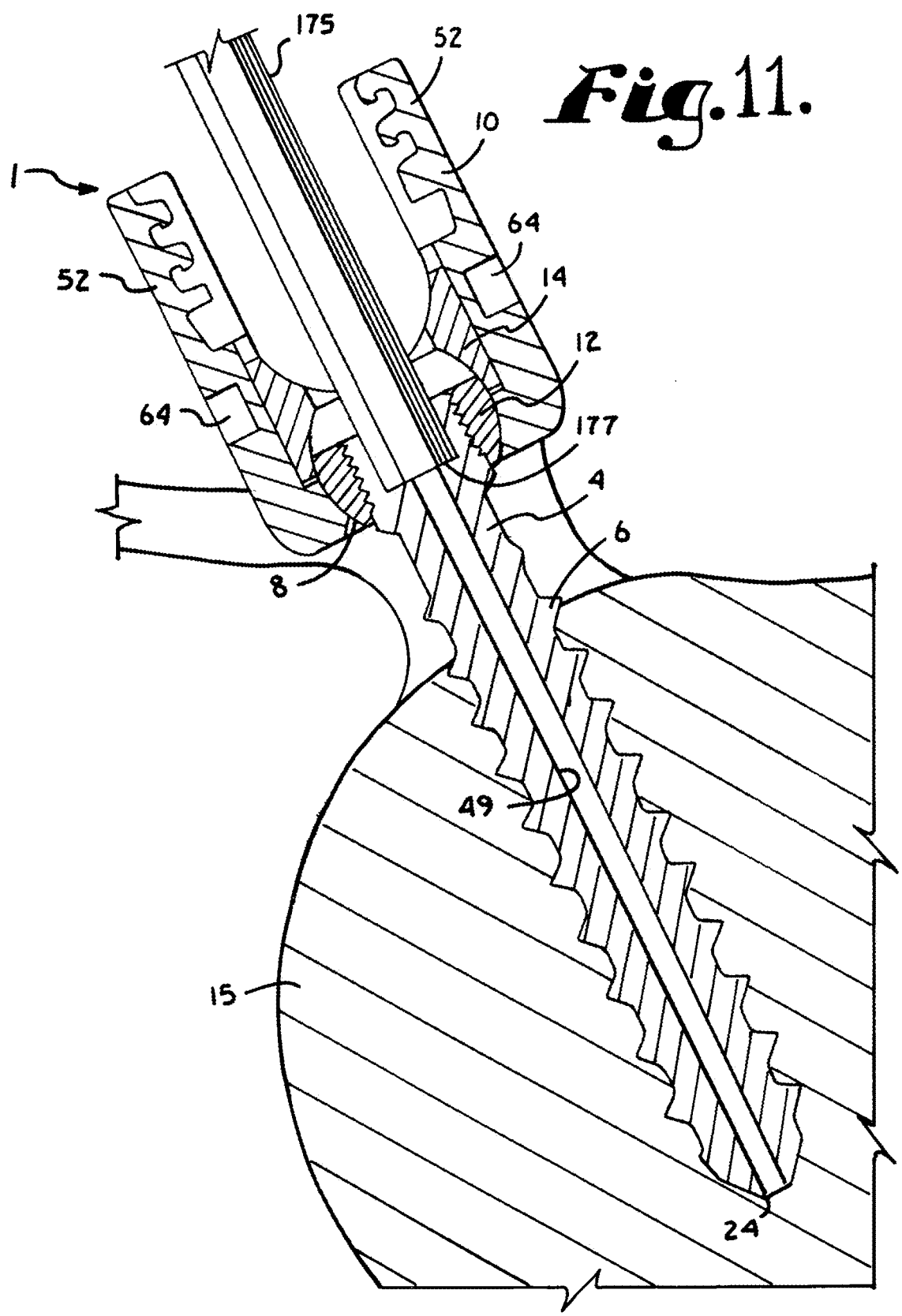
FIG. 11 is a cross-sectional view of the receiver, shank, retaining and articulating structure and compression structure, shown being driven into a vertebra with an Allen-type tool.

With reference to FIGS. 1-14, the reference numeral 1 generally designates a polyaxial bone screw assembly according to the present invention. The assembly 1 includes a shank 4 that further includes a body 6 integral with an upwardly extending, substantially cylindrical end or capture structure 8; a receiver or head 10; a retaining and articulating structure 12; and a compression structure 14. The shank 4, the receiver 10, the retaining and articulating structure 12 and the compression structure 14 are preferably assembled prior to implantation of the shank body 6 into a vertebra 15, which procedure is shown in FIG. 11 and will be discussed more fully below.

Figure 14:
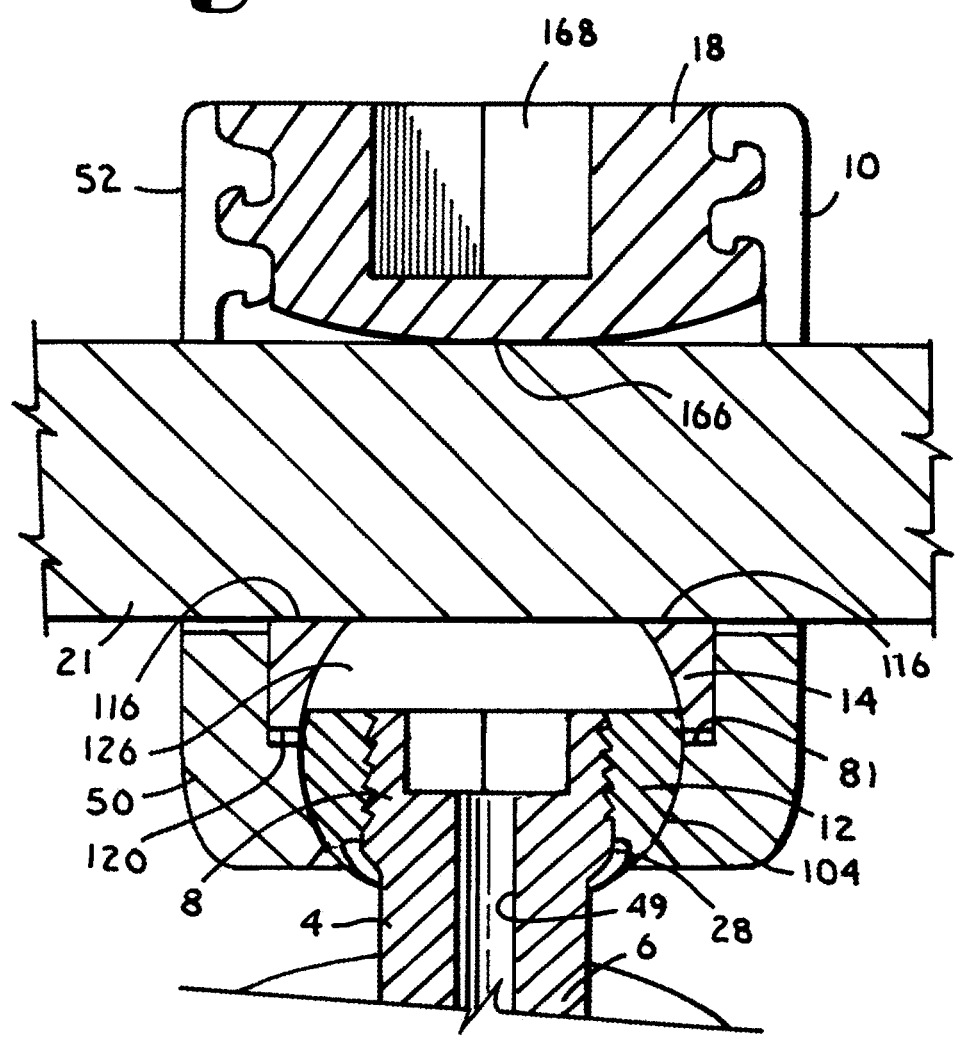
FIG. 14 is an enlarged and partial cross-sectional view taken along the line 14-14 of FIG. 13.

FIGS. 12-14 further show a closure structure generally 18, of the invention for capturing a longitudinal member such as a rod 21 within the receiver 10. Upon installation, which will be described in detail below, the closure structure 18 presses against the rod 21 that in turn presses against the compression structure 14 that presses against the retaining and articulating structure 12 that is threadably mated to the capture structure 8. The compression structure 14 biases the retaining and articulating structure 12 into fixed frictional contact with the receiver 10, so as to fix the rod 21 relative to the vertebra 15. The receiver 10, shank 4, retaining and articulating structure 12 and compression structure 14 cooperate in such a manner that the receiver 10 and shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other.

The shank 4, best illustrated in FIGS. 1 and 5-7, is elongate, with the shank body 6 having a helically wound, radially outwardly extending bone implantable thread 22 axially extending from near a tip 24 of the body 6 to near a slanted or sloped surface 26 that is adjacent to a lateral projection illustrated as a smooth cylindrical surface 28 located adjacent to the capture structure 8. As will be described more fully below, the laterally projecting cylindrical surface 28 includes a buttress stop feature 30 for frictional engagement with and placement of the retaining and articulating structure 12. During use, the body 6 utilizing the thread 22 for gripping and advancement is implanted into the vertebra 15 leading with the tip 24 and driven down into the vertebra 15 with an installation or driving tool so as to be implanted in the vertebra 15 to near the sloped surface 26, as shown in FIGS. 12-14, and as is described more fully in the paragraphs below. The shank 4 has an elongate axis of rotation generally identified by the reference letter A. It is noted that any reference to the words top, bottom, up and down, and the like, in this application refers to the alignment shown in the various drawings, as well as the normal connotations applied to such devices, and is not intended to restrict positioning of the assembly 1 in actual use.

The sloped surface 26 extends radially outward and axially upward from the shank body 6 to the cylindrical projection 28. Further extending axially from the projection 28 is the capture structure 8 that provides a connective or capture apparatus disposed at a distance from the threaded shank body 6 and thus at a distance from the vertebra 15 when the body 6 is implanted in the vertebra 15.

The capture structure 8 is configured for connecting the shank 4 to the receiver 10 and capturing the shank 4 in the receiver 10. The capture structure 8 has an outer substantially cylindrical surface 34 having a helically wound guide and advancement structure thereon which in the illustrated embodiment is a V-shaped thread 36 extending from adjacent the cylindrical surface 28 to adjacent an annular upper surface 38. The upper surface 38 is disposed substantially perpendicular to the axis of rotation A. A diameter of the cylindrical surface 34 measured between roots of the thread 36 is smaller than a diameter of the projected cylindrical surface 28. A diameter measured between crests of the thread 36 is illustrated equal to and may be smaller than the diameter of the cylindrical surface 28. Although a simple thread 36 is shown in the drawings, it is foreseen that other structures including other types of threads, such as buttress, square and reverse angle threads, and non threads, such as helically wound flanges with interlocking surfaces, may be alternatively used in place of the thread 36 in alternative embodiments of the present invention.

With particular reference to FIG. 7, the buttress stop feature 30 disposed near a base or bottom of the thread 36 is defined in part by the cylindrical surface 28 and in part by an upper shoulder 40 disposed perpendicular to the surface 28 and extending inwardly radially toward the thread 36. In a preferred embodiment, a buttress stop feature 42 disposed on the retaining and articulating structure 12 cooperates with the feature 30 as will be described more fully below to stop the advancement of the structure 12 along the thread 36 and provide for a desired placement of the structure 12 with respect to the capture structure 8.

A driving formation 44 extends from the upper surface 38 into the capture structure 8. The illustrated formation 44 includes six walls or facets 46 disposed parallel to the axis A and a hex-shaped seating surface or base 48 disposed perpendicular to the axis A. The driving formation 44 is sized and shaped to cooperate with a hex-driver for rotating and driving the shank body 6 into bone. It is foreseen that other driving features or apertures, such as slotted, tri-wing, hexalobular (such as the 6-point star shaped pattern sold under the trademark TORX), spanner, or the like may also be utilized according to the invention.

In the illustrated embodiment, the shank 4 is cannulated with a small central bore 49 extending an entire length of the shank along axis A. The bore 49 is coaxial with the threaded body 6 and the capture structure outer surface 34, providing a passage through the shank interior for a length of wire or pin inserted into the vertebra 15 prior to the insertion of the shank body 6, the wire or pin providing a guide for insertion of the shank body 6 into the vertebra 15.

Referring to FIGS. 1, and 8-10, the receiver 10 has a generally cylindrical outer profile with a substantially cylindrical base 50 integral with a pair of opposed upstanding arms 52 that extend from the base 50 to a top surface 54. The arms 52 form a U-shaped cradle and define a U-shaped channel 56 between the arms 52 and include an upper opening 57 and a lower seat 58 having substantially the same radius as the rod 21 for operably snugly receiving the rod 21.

Each of the arms 52 has an interior surface 60 that defines an inner cylindrical profile and includes a partial helically wound guide and advancement structure 62. In the illustrated embodiment, the guide and advancement structure 62 is a partial helically wound flangeform configured to mate under rotation with a similar structure on the closure top 18, as described more fully below. However, it is foreseen that the guide and advancement structure 62 could alternatively be a buttress thread, square thread, a reverse angle thread or other thread like or non-thread like helically wound advancement structures for operably guiding under rotation and advancing the closure top 18 downward between the arms 52 and having such a nature as to resist splaying of the arms 52 when the closure top 18 is advanced into the U-shaped channel 56.

Tool engagement apertures 64 are formed on outer substantially cylindrical surfaces 66 of the arms 52 which may be used for holding the receiver 10 with a holding tool (not shown) having projections that are received within the apertures 64 during implantation of the shank body 6 into the vertebra 15. The apertures 64 may also cooperate with a holding tool during bone screw assembly and during subsequent installation of the rod and closure top. The illustrated apertures 64 are circular and disposed centrally on each arm 52. However, it is foreseen that the apertures may be configured in a variety of shapes and sizes and include undercut surfaces and be disposed at other locations on the arms 52, including near the top surfaces 54. Also, the holding tool (not shown) and respective apertures 64 may be configured to provide for a variety of ways to install the holding tool in the apertures, including a twist on/twist off engagement with the receiver, a twist on/snap off engagement or a flexible snap on/snap off engagement wherein the holding tool has legs which splay outwardly to position the tool for engagement in the apertures 64 or a combination thereof.

Communicating with the U-shaped channel 56 and located within the base 50 of the receiver 10 is a chamber or cavity 78 partially defined by an inner cylindrical surface 80, the cavity 78 opening upwardly into the U-shaped channel 56. In the illustrated embodiment, the cylindrical surface 80 has a diameter equal to an inner diameter between the arms 52 measured between crests of the guide and advancement structure 62. In the illustrated embodiment, the cylindrical inner surface 80 terminates at a ledge or lower shoulder 81 that is disposed perpendicular to an axis of rotation B of the receiver. The shoulder 81 is adjacent to a partial internal spherical seating surface 82 having a first radius. The surface 82 is sized and shaped for mating with the retaining and articulating structure 12, as described more fully below. It is foreseen that the surface 82 may be partially spherical or conical, or the like, and may include a high friction surface.

The base 50 further includes a restrictive neck 83 adjacent the seating surface 82. The neck 83 defines a bore 84 communicating with the cavity 78 and a lower exterior 86 of the base 50. The bore 84 is coaxially aligned with respect to the rotational axis B of the receiver 10. The bore 84 may be conically counterbored or beveled in a region 87 to widen the angular range of the shank 4. The neck 83 and associated bore 84 are sized and shaped to be smaller than a radial dimension of a fixed or fully expanded retaining and articulating structure 12, as will be discussed further below, so as to form a restriction at the location of the neck 83 relative to the retaining and articulating structure 12, to prevent the structure 12 from passing from the cavity 78 and out into the lower exterior 86 of the receiver 10 when the retaining and articulating structure 12 is seated on the seating surface 82. Again, it is foreseen that the retaining and articulating structure could be compressible (such as where such structure has a missing section) and could be loaded through the neck 83 and then allowed to expand and fully seat in the spherical seating surface 82.

The retaining and articulating structure 12, best illustrated by FIGS. 1 and 5-7, has an operational central axis that is the same as the elongate axis A associated with the shank 4, but when the structure 12 is separated from the shank 4, the axis of rotation is identified as an axis C. The retaining and articulating structure 12 has a central bore 90 that passes entirely through the structure 12 from a top surface 92 to a bottom surface 94 thereof. An inner cylindrical surface 96 defines a substantial portion of the bore 90, the surface 96 having a helically wound guide and advancement structure thereon as shown by a v-shaped helical rib or thread 98 extending from adjacent the top surface 92 to near the bottom surface 94. Although a simple helical rib 98 is shown in the drawings, it is foreseen that other helical structures including other types of threads, such as buttress and reverse angle threads, and non threads, such as helically wound flanges with interlocking surfaces, may be alternatively used in an alternative embodiment of the present invention. The inner cylindrical surface 96 with the thread 98 are configured to mate under rotation with the capture structure outer surface 34 and helical guide and advancement structure or thread 36, as described more fully below.

The buttress stop formation 42 of the retaining and articulating structure 12 that is sized and shaped to mate with the stop 30 located on the shank 4 is located axially between the helical rib 98 and the bottom surface 94 of the structure 12. The formation 42 includes a lower shoulder 100 extending radially from the thread 98 and towards the structure 12 and a cylindrical wall 102 disposed perpendicular to the lower shoulder 100. The lower shoulder 100 is sized and shaped to mate and abut with the upper shoulder 40 and the cylindrical wall 102 is sized and shape to mate with the cylindrical projection 28. Thus, as will be described in more detail below, when the retaining and articulating structure 12 is rotated and mated with the capture structure 8 and fully installed thereon, the lower shoulder 100 of the structure 12 abuts the upper shoulder 40 of the stop 30. The retaining and articulating structure 12 and the capture structure 8 are configured such that when the buttress stop 30 abuts the buttress stop 42, the top surface 92 of the structure 12 is flush with the upper surface 38 of the capture structure 8. A sloped surface or chamfer 103 runs between the cylindrical wall 102 and the bottom surface 94 of the retaining and articulating structure 12.

It is foreseen that other types of geometrical orientation or structure may be utilized to engage or mate the capture structure and the retaining and articulating structure. For example, the capture structure may have an outer surface that is frusto-conical and the retaining and articulating structure may be a split ring with an inner surface sized and shaped to frictionally engage the frusto-conical capture structure. Also, the capture structure may have an inverted polyhedral or conical geometry and the mating retaining and articulating structure may be a plurality of pieces, the geometry of the pieces corresponding and cooperating with the polyhedral or conical geometry of the capture structure to frictionally envelope the retaining and articulating structure between the capture structure and an internal surface defining a cavity of the receiver.

The illustrated retaining and articulating structure 12 has a radially outer partially spherically shaped surface 104 sized and shaped to mate with the partial spherically shaped seating surface 82 of the receiver and having a radius approximately equal to the radius associated with the surface 82. The retaining and articulating structure radius is larger than the radius of the neck 83 of the receiver 10. Although not required, it is foreseen that the outer partially spherically shaped surface 104 may be a high friction surface such as a knurled surface or the like.

It is also foreseen that the retaining and articulating structure outer surface may be elliptical or ellipsoid in shape rather than spheroid in shape. Such an elliptical surface would be sized and shaped to contact and seat within a substantially spherical seating surface, such as the seating surface 82. Such an ellipsoid structure may be attachable to the shank upper portion by threads, a pin, compression, or the like as previously described with respect to the substantially spherical retaining and articulating structure 12. Furthermore, it is foreseen that an ellipsoid retaining structure may be integral with the bone screw shank and may include threads that allow the ellipsoid to be threadably received into a base of a bone screw receiver.

The illustrated retaining and articulating structure top surface 92 extends from the central bore 90 to the outer surface 104. The top surface 92 is disposed perpendicular to the axis of rotation C of the structure 12. The bottom surface 94 extends from the chamfer 103 to the outer surface 104 and also is disposed perpendicular to the axis of rotation C.

The elongate rod or longitudinal member 21 that is utilized with the assembly 1 can be any of a variety of implants utilized in reconstructive spinal surgery, but is normally a cylindrical elongate structure having a smooth, outer cylindrical surface 108 of uniform diameter. The rod 21 is preferably sized and shaped to snugly seat near the bottom of the U-shaped channel 56 of the receiver 10 and, during normal operation, is positioned slightly above the bottom of the channel 56 at the lower seat 58.

The compression structure 14 is best illustrated in FIGS. 1-4. In the embodiment shown, the compression structure 14 includes a body 110 of substantially circular cross-section integral with a pair of upstanding arms 112. The body 110 and arms 112 form a generally U-shaped, open, through-channel 114 having a substantially U-shaped bottom seating surface 116 having a radius substantially conforming to a radius of the rod 21 and thus configured to operably snugly engage the rod 21. The arms 112 disposed on either side of the channel 114 each included a top surface 118 that is parallel to an annular bottom surface 120. The compression structure 14 includes a substantially cylindrical outer surface 122 and an inner cylindrical wall 124 defining a central through-bore 125 extending along a central axis D of the compression structure 14. The top surface 118 and the bottom surface 120 are disposed perpendicular to the axis D. Extending between the inner cylindrical wall 124 and the bottom surface 120 is a curved or spherical surface 126 sized and shaped to frictionally engage and mate with the outer spherical surface 104 of the retaining and articulating structure 12. The cylindrical surface 122 has a diameter slightly smaller than a diameter between crests of the guide and advancement structure 62 allowing for top loading of the compression structure 14 as illustrated in FIGS. 8-10. The cylindrical surface 122 diameter and a height of the compression structure 14 measured from the top surface 118 to the bottom surface 120 are sized such that the compression structure 14 is received within the cylindrical surface 80 of the receiver 10 below the guide and advancement structure 62, but the bottom surface 120 thereof does not engage the ledge 81 when fully installed on the retaining and articulating structure 12. There is thus a space between the bottom surface 120 and the ledge 81 in any angular position of the shank 4 with respect to the receiver 10. When fully installed, the compression structure 14 does not contact the bone screw shank capture structure 8, but engages only with the retaining and articulating structure 12. When pressed upon by the rod 21, the surface 126 of the compression structure 14 frictionally engages the surface 104 of the retaining and articulating structure 12, which in turn presses upon the seating surface 82 of the receiver 10. In some embodiments, the compression structure could be up-loaded into the receiver, followed by up-loading of the retaining structure into the receiver.

With particular reference to FIGS. 12-14, the closure structure 18 can be any of a variety of different types of closure structures for use in conjunction with the present invention with suitable mating structure on the upstanding arms 52 of the receiver 10. The closure structure 18 is rotatable between the spaced arms 52. The illustrated structure 18 includes a cylindrical base 140 and a break-off head 142. Helically wound about the base 140 is a guide and advancement structure in the form of a flange form 144. The illustrated guide and advancement structure 144 operably joins with the guide and advancement structure 62 disposed on the interior 60 of the arms 52. The flange form 144 includes a root 146 and a crest 148. Furthermore, the flange form 144 also has a trailing surface 150 and a leading surface 152 which are relative to the forward movement of the closure 18 as it is rotated clockwise about the central axis B of the bone screw receiver and joined therewith. Located on the trailing surface 150 or the leading surface 152 or both is a projection which protrudes rearwardly or frontwardly with respect to the width of the flange form 144 at the root 146 and which interlocks with the guide and advancement mating structure 62 of the receiver 10.

In the illustrated embodiment, the flange form 144 has a protrusion 154 that projects rearwardly from the trailing surface 150. The flange form 144 utilized in accordance with the present invention may be any structure which effectively locks the closure 18 to the structure within which it is set so as to prevent splaying of the structure upon which mating guide and advancement structure is mounted. Various flange form structures which can be used alternatively are illustrated in applicant's U.S. Pat. No. 6,726,689, which is incorporated herein by reference. As stated herein with respect to the flange form guide and advancement structure 62, it is also foreseen that according to the invention the guide and advancement structure 144 could alternatively be a buttress thread, a square head, a reverse angle thread or other thread like or non-thread like helically wound advancement structure for operably guiding under rotation and advancing the closure 18 downward between the arms 52 and having such a nature as to resist splaying of the arms 52 when the closure top 18 is advanced into the U-shaped channel 56.

The base 140 of the closure structure 18 includes a lower surface 156 having a dome 158 located thereon. The dome 158 extends greatest from the base 140 along a central axis E that is operably coaxial with the receiver axis B. The dome 158 in the present embodiment is spherical in shape and, in particular, is a partial sphere that has a uniform or constant radius of generation.

However, it is foreseen that in certain embodiments the radius may vary depending upon the needs and desires of the particular structure and the dome 158 may have shape that is only partly a spherical curved surface or some other shape. The dome 158 may be a simple curved surface that allows greatest projection along the axis. That is, the dome surface could be radiused at the location of greatest projection and feathered along the periphery so as to not have a continuous uniform radius of generation throughout, but rather a continually changing radius of generation along at least the length thereof. Preferably, the dome 158 is smoothly curved where the dome 158 intersects with the axis E. It is also foreseen that the lower surface 156 could be flat or have a point and rim geometry.

The closure structure 18 break off head 142 is secured to the base 140 by a break off region 160 that is designed to allow the head 142 to break from the base 140 at a preselected torque, for example, 70 to 140 inch pounds. The break off head 142 has an external radial outward surface with six planar facets 162 so as to form a structure designed to be received within a socket of a driving type tool (not shown) with a similar receiving shape. The break off head 142 has a central bore 164 that may also include driving formations suitable for engagement by a tool (not shown).

During installation, the dome 158 engages the rod 21 at an apex 166 as seen in FIGS. 13 and 14. The closure structure 18 is torqued until a preselected pressure is reached at which point the closure 18 at the apex 166 abuts the rod 21 which in turn is urged toward but not completely to the lower seat 58 of the channel 56. In turn, the rod 21 braces against the compression structure 14 which urges the retaining and articulating structure 12 to fixedly seat in the cavity 78. Thereafter, the receiver 10 is no longer rotatable relative to the shank 4, but rather is locked in position.

The closure structure 18 also includes removal tool engagement structure which in the present embodiment is in the form of a hex-shaped and axially aligned aperture 168 disposed in the base 140, as shown in FIG. 13. The hex aperture 168 is accessible after the break-off head 142 breaks away from the base 140. The aperture 168 is coaxial with the helically wound guide and advancement structure 144 and is designed to receive a hex tool, of an Allen wrench type, into the aperture 168 for rotating the closure structure base 140 subsequent to installation so as to provide for removal thereof, if necessary. Although a hex-shaped aperture 168 is shown in the drawings, the tool engagement structure may take a variety of tool-engaging forms and may include more than one aperture of various shapes, such as a pair of spaced apertures, a left hand threaded bore, an easy out engageable step down bore or the like.

With reference to FIG. 1, prior to the polyaxial bone screw assembly 1 being implanted in the vertebra 15, the retaining and articulating structure 12 is typically first inserted or top-loaded, into the receiver U-shaped channel 56, and then into the cavity 78 to dispose the structure 12 adjacent the inner surface 80 of the receiver 10. The structure 12 may be loaded with the axis C coaxial with the receiver axis B or turned or rotated such that the axis C is perpendicular to the axis B of the receiver 10 during insertion of the structure 12 into the receiver 10. Then, after the retaining and articulating structure 12 is within the cavity 78, the retaining and articulating structure 12 is rotated approximately 90 degrees such that the axis C is coaxial with the axis B of the receiver 10, and then the structure 12 is seated in sliding engagement with the seating surface 82 of the receiver 10.

The shank capture structure 8 is preloaded, inserted or bottom-loaded into the receiver 10 through the bore 84 defined by the neck 83. The retaining and articulating structure 12, now disposed in the receiver 10 is coaxially aligned with the shank capture structure 8 so that the helical v-shaped thread 36 rotatingly mates with the thread 98 of the retaining and articulating structure 12.

With reference to FIGS. 5-7, the shank 4 and/or the retaining and articulating structure 12 are rotated to fully mate the structures 36 and 98 along the respective cylindrical surfaces 34 and 96, fixing the capture structure 8 to the retaining and articulating structure 12, until the lower shoulder 100 of the buttress stop 42 abuts the upper shoulder 40 of the stop 30.

With reference to FIGS. 8-10, at this time the shank 4 is in slidable and rotatable engagement with respect to the receiver 10, while the capture structure 8 and the lower aperture or neck 83 of the receiver 10 cooperate to maintain the shank body 6 in rotational relation with the receiver 10. According to the illustrated embodiment, only the retaining and articulating structure 12 is in slidable engagement with the receiver spherical seating surface 82. Both the capture structure 8 and threaded portion of the shank body 6 are in spaced relation with the receiver 10. The shank body 6 can be rotated through a substantial angular rotation relative to the receiver 10, both from side to side and from front to rear so as to substantially provide a universal or ball joint wherein the angle of rotation is only restricted by engagement of the neck 26 of the shank body 6 with the neck or lower aperture 83 of the receiver 10.

In the embodiment shown, the compression structure 14 illustrated in FIGS. 1-4 is then loaded into the receiver 10 as illustrated in FIGS. 8-10. With particular reference to FIG. 8, the insert U-shaped channel 114 is aligned with the receiver 10 U-shaped channel 56 and the compression structure 14 is initially top or down-loaded into the receiver 10 until the arms 112 are disposed adjacent to the surface 80 and the bottom spherical surface 126 is in contact with the surface 104 of the retaining and articulating structure 12. To ready the assembly 1 for implantation into bone, the shank 4, receiver 10 and compression structure 14 axes A, B and D, respectively are aligned, providing access to the hex-shaped formation 44 on the shank capture structure 8 through the bore 125 of the compression structure 14. Such placement allows for unrestricted rotation of the shank body 6 with respect to the receiver 10.

With reference to FIG. 11, the assembly 1 is typically screwed into a bone, such as the vertebra 15, by rotation of the shank 4 using a driving tool with an Allen type driving formation 175 that operably drives and rotates the shank 4 by engagement thereof with the shank at the driving formation 44, a base 177 of the tool 175 abutting and engaging the driving formation 44 at the base 48 thereof. It is foreseen that in other embodiments according to the invention, the hex-shaped driving formation 44 may be replaced by other types of foot print type tool engaging formations or recesses. Through the driving formation aperture, the retaining structure and the shank can be crimped together so as to not come apart with rotation.

Typically at least two and up to a plurality of bone screw assemblies 1 are implanted into vertebrae for use with the rod 21. Each vertebra 15 may be pre-drilled to minimize stressing the bone. Furthermore, when a cannulated bone screw shank is utilized, each vertebra will have a guide wire or pin (not shown) inserted therein that is shaped for the bone screw cannula 49 of the bone screw shank and provides a guide for the placement and angle of the shank 4 with respect to the vertebra 15. A further tap hole may be made using a tap. The shank body 6 is then driven into the vertebra 15, by rotation of the driving tool 175.

With reference to FIGS. 12-14, the rod 21 is eventually positioned within the receiver U-shaped channel 56, and the closure structure is then inserted into and advanced between the arms 52. The compression structure 14 is pressed downwardly into engagement with the retaining and articulating structure outer surface 104 to set the angle of articulation of the shank body 6 with respect to the receiver 10 by pressure from the rod 21 that in turn is being pressed upon by the dome 158 of the closure structure 18. The rod 21 is seated on the compression structure 14 and the fastener 18 is initially placed between the arms 52 and rotated using an installation tool (not shown) engaged with the surfaces 162 of the break-off head 142 until the guide and advancement structure 144 is fully mated with the receiver guide and advancement structure 62. With reference to FIG. 13, the break-off head 142 is then twisted to a preselected torque, for example 70 to 140 inch pounds, also utilizing the installation tool in engagement with the faceted outer surface 162 of the break-off head 142, with or without bending of the rod 21 in order to achieve and maintain a desired alignment of the spine. As illustrated in FIGS. 13 and 14, upon final installation, a stable fixation of the rod 21 is accomplished with one area of contact provided at the apex 166 of the closure top dome 158 and two areas of contact provided between the rod 21 and the compression structure 14.

If removal of the assembly 11 is necessary, or if it is desired to release the rod 21 at a particular location, disassembly is accomplished by using an Allen type tool (not shown) with the hex-shaped driving formation 168 located on the closure structure base 140 to rotate and remove the closure structure base 140 from the receiver 10. Disassembly of the assembly 1 is accomplished in reverse order to the procedure described previously herein for assembly. Again, it is foreseen that a non-break off closure could be used which is inserted and removed with the same driving formation.

It is to be understood that while certain forms of the present invention have been illustrated and described herein, it is not to be limited to the specific forms or arrangement of parts described and shown.

What is claimed is:

1. A pivotal bone anchor assembly configured for implantation into a bone of a patient about a guide wire with a drive tool, and for securing a fixation rod to the bone with a fastener configured to apply a downwardly-directed force to lock the assembly, the pivotal bone anchor assembly comprising:
    a shank comprising a longitudinal axis, an anchor portion at a distal end configured for fixation to the bone, and a proximal end portion including an upwardly-opening internal drive socket configured to mate with the drive tool, an upwardly-facing planar top surface perpendicular to the longitudinal axis surrounding and entirely peripheral to the internal drive socket, and a partially spherical lower surface curving upwardly and outwardly from a neck portion that extends between the proximal end portion and the anchor portion, the shank including a central bore centered about the longitudinal axis and extending distally from the internal drive socket to a distal tip of the anchor portion and configured to receive the guide wire;
    a receiver comprising a base portion defining an axial bore centered about a vertical centerline axis and an upper portion integral with the base portion defining a through channel configured to receive the fixation rod, the axial bore communicating with a bottom of the receiver through a lower opening and extending upward through the channel to a top of the receiver, the axial bore including a guide and advancement structure adjacent the top of the receiver configured to mate with the fastener and a partially spherical engagement surface adjacent the lower opening configured to pivotably receive the partially spherical lower surface of the proximal end portion of the shank with the shank extending downward through the lower opening; and
    an insert positionable within the axial bore of the receiver having an upper surface configured to engage the fixation rod, a lower surface configured to transfer the downwardly-directed force toward the proximal end portion of the shank to lock the assembly, and a central aperture configured to provide access to the internal drive socket for the drive tool,
    wherein after the proximal end portion of the shank and the insert are positioned in the axial bore of the receiver, the planar top surface on the proximal end portion is configured to remain spaced apart from the lower surface of the insert so as to not directly receive the downwardly-directed force when the assembly is locked by the fastener.

2. The pivotal bone anchor assembly of claim 1, wherein the proximal end portion of the shank is configured for positioning within the axial bore of the receiver prior to the insert.

3. The pivotal bone anchor assembly of claim 1, wherein the central bore of the shank defines a closed surface along an entire length thereof.

4. The pivotal bone anchor assembly of claim 1,
    wherein the internal drive socket further comprises an internal drive aperture with interior sidewalls extending downward from a top of the proximal end portion to a bottom abutment surface configured for engagement by the drive tool, and
    wherein the central bore of the shank further comprises an upper opening communicating with the bottom abutment surface of the internal drive aperture so as to allow the guide wire to pass therethrough.

5. The pivotal bone anchor assembly of claim 1, wherein the upwardly-facing planar top surface includes a substantially circular outer edge.

6. The pivotal bone anchor assembly of claim 1, wherein the neck portion of the shank has a substantially smooth outer surface.

7. The pivotal bone anchor assembly of claim 1, wherein the through channel of the receiver further comprises an upwardly-open channel defined by inner surfaces of a pair of upright arms extending upwardly from the base portion.

8. The pivotal bone anchor assembly of claim 7, wherein the guide and advancement structure of the axial bore of the receiver further comprises a discontinuous helically wound guide and advancement structure configured to resist splaying of the pair of upright arms upon mating with the fastener.

9. The pivotal bone anchor assembly of claim 8, wherein the discontinuous helically wound guide and advancement structure is a buttress thread.

10. The pivotal bone anchor assembly of claim 8, wherein the discontinuous helically wound guide and advancement structure is a square thread.

11. The pivotal bone anchor assembly of claim 8, wherein the discontinuous helically wound guide and advancement structure is a reverse angle thread.

12. The pivotal bone anchor assembly of claim 1, wherein the insert is configured to be spaced apart from the fastener when the fixation rod is positioned within the through channel of the receiver and against the upper surface of the insert and the pivotal bone anchor assembly is locked with the fastener.

13. The pivotal bone anchor assembly of claim 1, wherein the upper surface of the insert further comprises a U-shaped through channel defined by a pair of upstanding arms, the upstanding arms having uppermost top surfaces configured to be positioned below a midpoint of the fixation rod when the fixation rod is positioned within the channel of the receiver and against the U-shaped through channel of the insert and the pivotal bone anchor assembly is locked with the fastener.

14. The pivotal bone anchor assembly of claim 1, wherein the insert is configured to have a non-snap-fit engagement with the fixation rod.

15. The pivotal bone anchor assembly of claim 1 and further comprising a retainer configured to capture and hold the proximal end portion of the shank within the axial bore of the receiver with the shank extending downward through the lower opening.

16. The pivotal bone anchor assembly of claim 15, wherein the retainer is positionable within the axial bore prior to the proximal end portion of the shank.

17. The pivotal bone anchor assembly of claim 1, wherein the partially spherical lower surface of the proximal end portion of the shank extends outwardly and upwardly from the neck portion to define a partially spherical outer surface formed integral with the shank and having a diameter great than a diameter of the lower opening so as to maintain the capture portion within the axial bore of the receiver with the shank extending downward through the lower opening.

18. The pivotal bone anchor assembly of claim 1 and further comprising the fixation rod and the fastener, wherein the fastener is configured for positioning within the axial bore of the receiver above the fixation rod positioned in the through channel, and for engagement with the guide and advancement structure to apply the downwardly-directed force towards a top of the fixation rod so as to frictionally lock the shank in a fixed position relative to the receiver.

19. A pivotal bone anchor assembly configured for implantation into a bone of a patient about a guide wire with a drive tool, and for securing a fixation rod to the bone with a fastener configured to apply a downwardly-directed force to lock the assembly, the pivotal bone anchor assembly comprising:
   a shank comprising a longitudinal axis, an anchor portion at a distal end configured for fixation to the bone, and a proximal end portion including an upwardly-opening internal drive socket configured to mate with the drive tool, an upwardly-facing planar top surface perpendicular to the longitudinal axis surrounding and entirely peripheral to the internal drive socket, and a partially spherical lower surface adjacent a neck portion that extends between the proximal end portion and the anchor portion, the shank including a central bore centered about the longitudinal axis and extending distally from the internal drive socket to a distal tip of the anchor portion and configured to receive the guide wire;
   a receiver comprising a base portion defining a lower portion of an axial bore centered about a vertical centerline axis and a pair of integral upright arms extending upwardly from the base portion to define a through channel configured to receive the fixation rod, the axial bore communicating with a bottom of the receiver through a lower opening and extending upward through the channel to a top of the receiver, the axial bore including a guide and advancement structure adjacent the top of the receiver configured to mate with the fastener and an internal support surface adjacent the lower opening configured to pivotably receive the partially spherical lower surface of the proximal end portion of the shank with the shank extending downward through the lower opening; and
   an insert positionable within the axial bore of the receiver having an upper surface configured to receive the fixation rod, a lower surface configured to transfer the downwardly-directed force toward the proximal end portion of the shank to lock the assembly, and a central aperture configured to provide access to the internal drive socket of the proximal end portion by the drive tool,
   wherein after assembly of the proximal end portion of the shank and the insert into the axial bore of the receiver, the planar top surface on the proximal end portion is configured to remain spaced apart from the lower surface of the insert so as to not directly receive the downwardly-directed force when the assembly is locked by the fastener.

20. The pivotal bone anchor assembly of claim 19, wherein the internal drive socket further comprises an internal tool aperture with interior sidewalls extending downward from a top of the proximal end portion to a bottom abutment surface configured for engagement by the drive tool, and
   wherein the central bore of the shank further comprises an upper opening communicating with the bottom abutment surface of the internal tool aperture.

21. The pivotal bone anchor assembly of claim 19, wherein the partially spherical lower surface of the proximal end portion of the shank extends outwardly and upwardly from the neck portion to define a partially spherical outer surface formed integral with the shank and having a diameter great than a diameter of the lower opening so as to maintain the capture portion within the axial bore of the receiver with the shank extending downward through the lower opening.

22. The pivotal bone anchor assembly of claim 19, wherein the upwardly-facing planar top surface includes a substantially annular outer edge.

23. The pivotal bone anchor assembly of claim 19 and further comprising a retainer configured to capture and hold the proximal end portion of the shank within the axial bore of the receiver, wherein the retainer is positionable within the axial bore prior to the proximal end portion of the shank.

24. The pivotal bone anchor assembly of claim 23, wherein a lower portion of an outer surface of the retainer is configured to slidably engage the internal support surface of the axial bore to pivotally support the proximal end portion of the shank prior to the assembly being locked by the fastener.

25. The pivotal bone anchor assembly of claim 23, wherein an upper portion of an outer surface of the retainer is configured to directly receive the downwardly-directed force from the lower surface of the insert when the assembly is locked by the fastener.

26. The pivotal bone anchor assembly of claim 23, wherein the planar top surface of the proximal end portion of the shank does not extend above a top surface of the retainer upon the capture of the proximal end portion by the retainer.

27. The pivotal bone anchor assembly of claim 23, wherein the retainer is configured to be top loaded into the axial bore of the receiver.

28. The pivotal bone anchor assembly of claim 23, wherein the retainer is configured to be bottom loaded into the axial bore of the receiver.

29. The pivotal bone anchor assembly of claim 23, wherein the retainer is configured for threaded engagement with the proximal end portion of the shank to capture and hold the proximal end portion within the axial bore of the receiver.

30. The pivotal bone anchor assembly of claim 23, wherein the proximal end portion of the shank is configured to be captured by the retainer within the axial bore of the receiver prior to the anchor portion of the shank being implanted in the bone about the guide wire with the drive tool.

31. The pivotal bone anchor assembly of claim 19 and further comprising the fixation rod and the fastener, wherein the fastener is configured for positioning within the axial bore of the receiver above the fixation rod positioned in the channel, and for engagement with the guide and advancement structure to apply the downwardly-directed force towards a top of the fixation rod so as to frictionally lock the shank in a fixed position relative to the receiver.

32. The pivotal bone anchor assembly of claim 19, wherein the insert is top loaded into the axial bore of the receiver.

33. The pivotal bone anchor assembly of claim 19, wherein an uppermost portion of the proximal end portion of the shank is devoid of vertically-extending cylindrical outer surfaces aligned parallel with respect to the longitudinal axis.

34. The pivotal bone anchor assembly of claim 19, wherein the receiver includes outwardly-facing lateral planar surfaces parallel with a centerline axis of the through channel and outwardly-facing front and back planar surfaces perpendicular to the lateral planar surfaces.

35. The pivotal bone anchor assembly of claim 34, wherein the lateral planar surfaces are recessed into an outer surface of the receiver.

36. The pivotal bone anchor assembly of claim 19, wherein the internal support surface adjacent the lower opening further comprises a partial spherical seating surface.

* * * * *